(12) United States Patent
Quinn

(10) Patent No.: US 9,308,115 B2
(45) Date of Patent: Apr. 12, 2016

(54) BODY-ADHESIVE KINESIOLOGY TAPE

(75) Inventor: Reed M. Quinn, Highland, UT (US)

(73) Assignee: KT HEALTH, LLC, Lindon, UT (US)

( * ) Notice: Subject to any disclaimer, the term of this patent is extended or adjusted under 35 U.S.C. 154(b) by 440 days.

(21) Appl. No.: 12/626,355

(22) Filed: Nov. 25, 2009

(65) Prior Publication Data

US 2010/0298747 A1 Nov. 25, 2010

Related U.S. Application Data

(60) Provisional application No. 61/200,400, filed on Nov. 26, 2008.

(51) Int. Cl.
*A61F 15/00* (2006.01)
*A61F 5/40* (2006.01)
*A61F 13/02* (2006.01)
*A61F 13/00* (2006.01)

(52) U.S. Cl.
CPC ............... *A61F 5/40* (2013.01); *A61F 13/023* (2013.01); *A61F 2013/0028* (2013.01); *A61F 2013/00919* (2013.01)

(58) Field of Classification Search
CPC ..... A61L 15/58; A61F 13/02; A61F 13/0253; A61F 13/0259; A61F 13/2073; B32B 27/12; B32B 2555/00; B32B 2307/51; B32B 5/024; C09J 2201/28; C09J 2201/40
USPC ............... 602/44, 52, 54, 55, 57, 58, 59, 903; 523/111, 105, 118, 112, 113, 114; 428/175, 193, 196, 214
See application file for complete search history.

(56) References Cited

U.S. PATENT DOCUMENTS

| 1,441,708 | A | 1/1923 | Overbury |
| 2,310,082 | A | 2/1943 | Holbrooke |
| 2,349,709 | A | 5/1944 | Evans |
| 2,399,545 | A | 4/1946 | Davis |
| 2,646,040 | A | 7/1953 | Stanton |

(Continued)

FOREIGN PATENT DOCUMENTS

| BE | 1002779 | 6/1991 |
| CN | 101616645 A | 12/2009 |

(Continued)

OTHER PUBLICATIONS

Kinesio Taping Perfect Manual.

(Continued)

*Primary Examiner* — Nicholas Woodall
*Assistant Examiner* — Caitlin Carreiro
(74) *Attorney, Agent, or Firm* — Maschoff Brennan

(57) ABSTRACT

The body-adhesive kinesiology tape includes a strip of kinesiology tape. The strip of kinesiology tape includes a first end and a second end where the second end is opposite the first end. The body-adhesive kinesiology tape also includes a longitudinal cut in the strip of kinesiology tape extending from the first end to a pre-determined distance from the second end and adhesive on a first surface of the strip of kinesiology tape. The adhesive is configured to adhere the strip of kinesiology tape to a human body. The body-adhesive kinesiology tape further includes a backing material on the first surface of the strip of kinesiology tape. The backing material is configured to cover the adhesive and protect the adhesive from drying until a user is ready to apply the strip of kinesiology tape to the human body.

17 Claims, 6 Drawing Sheets

(56) References Cited

U.S. PATENT DOCUMENTS

| | | | |
|---|---|---|---|
| 2,940,868 A | | 6/1960 | Patchell |
| 3,038,295 A | | 6/1962 | Humpreys |
| 3,199,548 A | | 8/1965 | Conant |
| 3,342,028 A | | 9/1967 | Kanji et al. |
| 3,355,974 A | | 12/1967 | Carmichael |
| 3,387,451 A | | 6/1968 | Cape et al. |
| 3,457,919 A | | 7/1969 | Harbard |
| 3,530,494 A | * | 9/1970 | Baratta ............ 206/441 |
| 3,618,754 A | | 11/1971 | Hoey |
| 3,716,132 A | | 2/1973 | Lewyckyj |
| 3,965,786 A | | 6/1976 | D'Luhy |
| 3,989,041 A | | 11/1976 | Davies |
| 4,215,687 A | | 8/1980 | Shaw |
| 4,428,809 A | | 1/1984 | Heimbach et al. |
| 4,654,254 A | | 3/1987 | Gerry et al. |
| 4,734,320 A | | 3/1988 | Ohira et al. |
| 4,735,342 A | * | 4/1988 | Goldstein ............ 221/25 |
| 4,782,196 A | | 11/1988 | Ukai |
| 4,807,753 A | * | 2/1989 | Goldstein ........... 206/390 |
| 5,230,701 A | | 7/1993 | Meyer et al. |
| 5,240,775 A | | 8/1993 | Tannenbaum |
| 5,397,298 A | | 3/1995 | Mazza et al. |
| 5,488,889 A | | 2/1996 | Kang |
| 5,496,605 A | * | 3/1996 | Augst et al. .......... 428/43 |
| 5,537,905 A | | 7/1996 | Zimmer et al. |
| 5,755,681 A | | 5/1998 | Plews |
| 5,782,496 A | | 7/1998 | Casper et al. |
| 5,792,091 A | * | 8/1998 | Staudinger .......... 602/57 |
| 5,861,348 A | * | 1/1999 | Kase ................ 442/184 |
| 5,938,631 A | | 8/1999 | Colma |
| 6,007,468 A | | 12/1999 | Giacometti |
| 6,213,343 B1 | * | 4/2001 | Damikolas ............ 221/25 |
| 6,422,848 B1 | | 7/2002 | Allen et al. |
| 6,756,519 B2 | * | 6/2004 | Johnson et al. ........ 602/58 |
| 6,849,057 B2 | | 2/2005 | Satou et al. |
| 6,953,602 B2 | * | 10/2005 | Carte et al. .......... 427/208.4 |
| 6,953,620 B2 | | 10/2005 | Schneider et al. |
| 7,012,170 B1 | * | 3/2006 | Tomaioulo ............ 602/57 |
| 7,146,893 B2 | | 12/2006 | Aichele |
| 7,419,476 B2 | | 9/2008 | Oohira et al. |
| 7,594,461 B2 | | 9/2009 | Aichele et al. |
| D604,856 S | | 11/2009 | Arbesman et al. |
| D607,114 S | | 12/2009 | Arbesman et al. |
| D608,007 S | | 1/2010 | Arbesman et al. |
| D608,453 S | | 1/2010 | Arbesman et al. |
| D608,893 S | | 1/2010 | Arbesman et al. |
| D608,894 S | | 1/2010 | Arbesman et al. |
| D608,896 S | | 1/2010 | Arbesman et al. |
| D609,354 S | | 2/2010 | Arbesman et al. |
| D612,505 S | | 3/2010 | Arbesman et al. |
| D612,506 S | | 3/2010 | Arbesman et al. |
| D612,507 S | | 3/2010 | Arbesman et al. |
| D612,508 S | | 3/2010 | Arbesman et al. |
| D612,944 S | | 3/2010 | Arbesman et al. |
| D613,414 S | | 4/2010 | Arbesman et al. |
| D613,415 S | | 4/2010 | Arbesman et al. |
| D616,553 S | | 5/2010 | Arbesman et al. |
| D616,998 S | | 6/2010 | Arbesman et al. |
| D621,518 S | | 8/2010 | Arbesman et al. |
| D622,403 S | | 8/2010 | Arbesman et al. |
| D625,422 S | | 10/2010 | Arbesman et al. |
| D625,825 S | | 10/2010 | Arbesman et al. |
| 8,216,415 B2 | | 7/2012 | Quinn |
| 2002/0040202 A1 | | 4/2002 | Levin |
| 2003/0069530 A1 | | 4/2003 | Satou et al. |
| 2003/0183053 A1 | | 10/2003 | Amend et al. |
| 2006/0065098 A1 | | 3/2006 | Cranna |
| 2007/0010777 A1 | | 1/2007 | Dunshee et al. |
| 2007/0212520 A1 | | 9/2007 | Furumori et al. |
| 2008/0154169 A1 | | 6/2008 | Kase |
| 2008/0299855 A1 | | 12/2008 | Morihashi |
| 2009/0182256 A1 | | 7/2009 | Lin |
| 2009/0192256 A1 | | 7/2009 | Takeda |
| 2010/0016771 A1 | | 1/2010 | Arbesman et al. |
| 2010/0227102 A1 | | 9/2010 | Keener et al. |
| 2010/0277102 A1 | | 11/2010 | Lin et al. |
| 2010/0298747 A1 | | 11/2010 | Quinn |

FOREIGN PATENT DOCUMENTS

| | | |
|---|---|---|
| DE | 825 448 C | 12/1952 |
| DE | 1221091 | 7/1996 |
| FR | 2 896 808 A1 | 8/2007 |
| GB | 953855 | 4/1964 |
| JP | 2004 248842 A | 9/2004 |
| JP | 2008-136656 | 6/2008 |
| WO | 2006067876 | 6/2006 |

OTHER PUBLICATIONS

Office Action from Chinese Patent Application 201280044120.0 dated Nov. 3, 2014.
U.S. Appl. No. 13/188,333, filed Jul. 21, 2011, Quinn.
U.S. Appl. No. 13/188,319, filed Jul. 21, 2011, Quinn.
U.S. Appl. No. 13/188,327, filed Jul. 21, 2011, Quinn.
U.S. Appl. No. 14/135,416, filed Dec. 19, 2013, Quinn.
Office Action from U.S. Appl. No. 13/188,319 dated May 6, 2014.
Office Action from U.S. Appl. No. 13/188,333 dated Jun. 9, 2014.
Office Action from U.S. Appl. No. 13/188,333 dated Sep. 14, 2012.
Office Action from U.S. Appl. No. 13/188,333 dated Oct. 8, 2013.
Office Action from U.S. Appl. No. 13/188,327 dated Nov. 8, 2013.
Office Action from U.S. Appl. No. 13/188,319, dated Dec. 11, 2014.
Office Action from Canadian Patent Application No. 2,845,061, dated Feb. 16, 2015.
Office Action from Korean Patent Application No. 10-2014-7004559, dated Jan. 6, 2015 (with English translation).
Supplemental European Search Report from EPO Appl. No. EP 12 81 4131 dated Mar. 12, 2015.
Office Action from Chinese Patent Application No. 201280044120.0 dated Sep. 6, 2015.
Office Action from U.S. Appl. No. 13/188,319 dated Sep. 28, 2015.
Examination Report from Australian Patent Application No. 2012285492 dated Jul. 15, 2015.

* cited by examiner

BODY-ADHESIVE KINESIOLOGY TAPE

CROSS-REFERENCE TO RELATED APPLICATIONS

This application claims the benefit of and priority to U.S. Provisional Patent Application Ser. No. 61/200,400, entitled "Body-Adhesive Kinesiology Tape for Sports and Medical Use and Methods and Processes Related Thereto" filed on Nov. 26, 2008, which application is incorporated herein by reference in its entirety.

BACKGROUND OF THE INVENTION

Kinesiology tape consists of a strip of elastic and non-elastic fibers, usually covered in cotton, which is placed on human skin. Kinesiology tape is useful in therapy to reduce soreness in overused and injured muscles and in rehabilitation to accelerate recovery. The tape can have a lifting effect on the skin which can reduce swelling and inflammation by improving circulation and reduce pain by taking pressure off pain receptors.

Nevertheless, there are a number of drawbacks in the current art regarding kinesiology tape. In particular, in order to provide proper support to various muscle groups or body parts, body-adhesive tapes must be applied in specific ways, which often requires that multiple strips of specific sizes and shapes be utilized. However, kinesiology tapes are generally available as a roll and the user must remove from the roll of tape the correct amount and, at times, cut the piece further, to allow the tape to properly support joints or muscles.

Body-adhesive kinesiology tapes for athletic use are required to be strong, resiliently elastic, and resistant to tearing in order to provide adequate support to a user. Such tapes cannot be easily torn into smaller pieces, but must be carefully cut into a desired size and shape. This requires that scissors be used to cut the tape into the desired shape and size. However, the scissors must be quite sharp, as the tape does not readily cut due to its elastic nature. This presents a danger to the user, as they may have to carry these scissors with them to the gym or other place of use.

Further, cutting the kinesiology tape can leave edges on the kinesiology tape with sharp corners. Since kinesiology tape is often used on or near joints, these sharp corners may continually poke or otherwise irritate the user. Moreover, the cut edges of the tape may begin to fray because of the cut. This may cause the kinesiology tape to become loose while the user is participating in some physical activity. Alternatively, the user may be required to reapply the kinesiology tape during some break in the activity to ensure that the tape does not become loose or fall off.

Additionally, different joints and muscle groups may require different applications of kinesiology tape. Indeed, one joint or muscle group may need different configurations of kinesiology tape for different injuries to the joint or muscle group. Therefore, the user may need to be aware of the proper method of application as well as the type and length of kinesiology tape to apply.

Thus, those with access to professional personnel, such as personal trainers or physical therapists are able to utilize the benefits of kinesiology tapes. However those without access to such personnel such as a person making a casual trip to the gym, or due to other time, location or access reasons are not able to enjoy these benefits.

This can prevent casual users from receiving the support benefits from such tapes. A casual user may lack the means to cut the tape and the knowledge of the different shapes and sizes of the particular strips of tape required to support a particular body area may not be readily apparent.

Accordingly, the design of a body adhesive kinesiology tape that could be applied in multiple useful conformations without the need for custom cutting and fitting would be an improvement in the art.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

One example embodiment includes body-adhesive kinesiology tape. The body-adhesive kinesiology tape includes a strip of kinesiology tape. The strip of kinesiology tape includes a first end and a second end where the second end is opposite the first end. The body-adhesive kinesiology tape also includes a longitudinal cut in the strip of kinesiology tape extending from the first end to a pre-determined distance from the second end and adhesive on a first surface of the strip of kinesiology tape. The adhesive is configured to adhere the strip of kinesiology tape to a human body. The body-adhesive kinesiology tape further includes a backing material on the first surface of the strip of kinesiology tape. The backing material is configured to cover the adhesive and protect the adhesive from drying until a user is ready to apply the strip of kinesiology tape to the human body.

Another example embodiment includes body-adhesive kinesiology tape. The body-adhesive kinesiology tape includes a strip of kinesiology tape. The strip of kinesiology tape is approximately rectangular in shape and includes rounded corners. The body-adhesive kinesiology tape also includes a longitudinal cut in the strip of kinesiology tape extending from a first edge of the strip of kinesiology tape to a pre-determined distance from a second edge of the strip of kinesiology tape where the first edge is opposite the second edge. The body-adhesive kinesiology tape further includes adhesive on a first surface of the strip of kinesiology tape. The adhesive is applied in a step frequency wave pattern and is configured to adhere the strip of kinesiology tape to a human body. The body-adhesive kinesiology tape also includes a backing material on the first surface of the strip of kinesiology tape. The backing material is configured to protect the adhesive from drying until a user is ready to apply the strip of kinesiology tape to the human body.

Yet another example embodiment includes body-adhesive kinesiology tape. The body-adhesive kinesiology tape includes two or more strips of kinesiology tape. The two or more strips of kinesiology tape are approximately rectangular in shape and include rounded corners. The body-adhesive kinesiology tape also includes adhesive on a first surface of each of the two or more strips of kinesiology tape. The adhesive is applied in a step frequency wave pattern and is configured to adhere each of the two or more strips of kinesiology tape to a human body. The body-adhesive kinesiology tape further includes a backing material. The backing material includes a perforation. The perforation is configured to permit a user to detach a first portion of the backing material from a second portion of the backing material. The backing material also includes at least one of the two or more strips of kinesiology tape adhered to the first portion of the backing material. The backing material further includes at least one of the two or more strips of kinesiology tape adhered to the second portion of the backing material.

These and other objects and features of the present invention will become more fully apparent from the following description and appended claims, or may be learned by the practice of the invention as set forth hereinafter.

BRIEF DESCRIPTION OF THE DRAWINGS

To further clarify various aspects of some example embodiments of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF SOME EXAMPLE EMBODIMENTS

Reference will now be made to the figures wherein like structures will be provided with like reference designations. It is understood that the figures are diagrammatic and schematic representations of some embodiments of the invention, and are not limiting of the present invention, nor are they necessarily drawn to scale.

In addition to providing support, body-adhesive kinesiology tapes are used by athletes for the enhancement of athletic performance and are used by athletes and non-athletes for the reduction of muscle soreness, to aid in healing from injury and in the prevention of injury. Upon application to body parts with the skin pulled taut, after returning the skin to an unstretched position the elastic properties of body-adhesive kinesiology tapes provide an outward stretching or "lifting" force on the skin, providing enhanced fluid flow from the taped area by assisting in the opening of the lymphatic system and microcapillaries in the subcutaneous layers. Additionally, this stretching force can provide a counterbalance to muscle strain.

Figure 1:
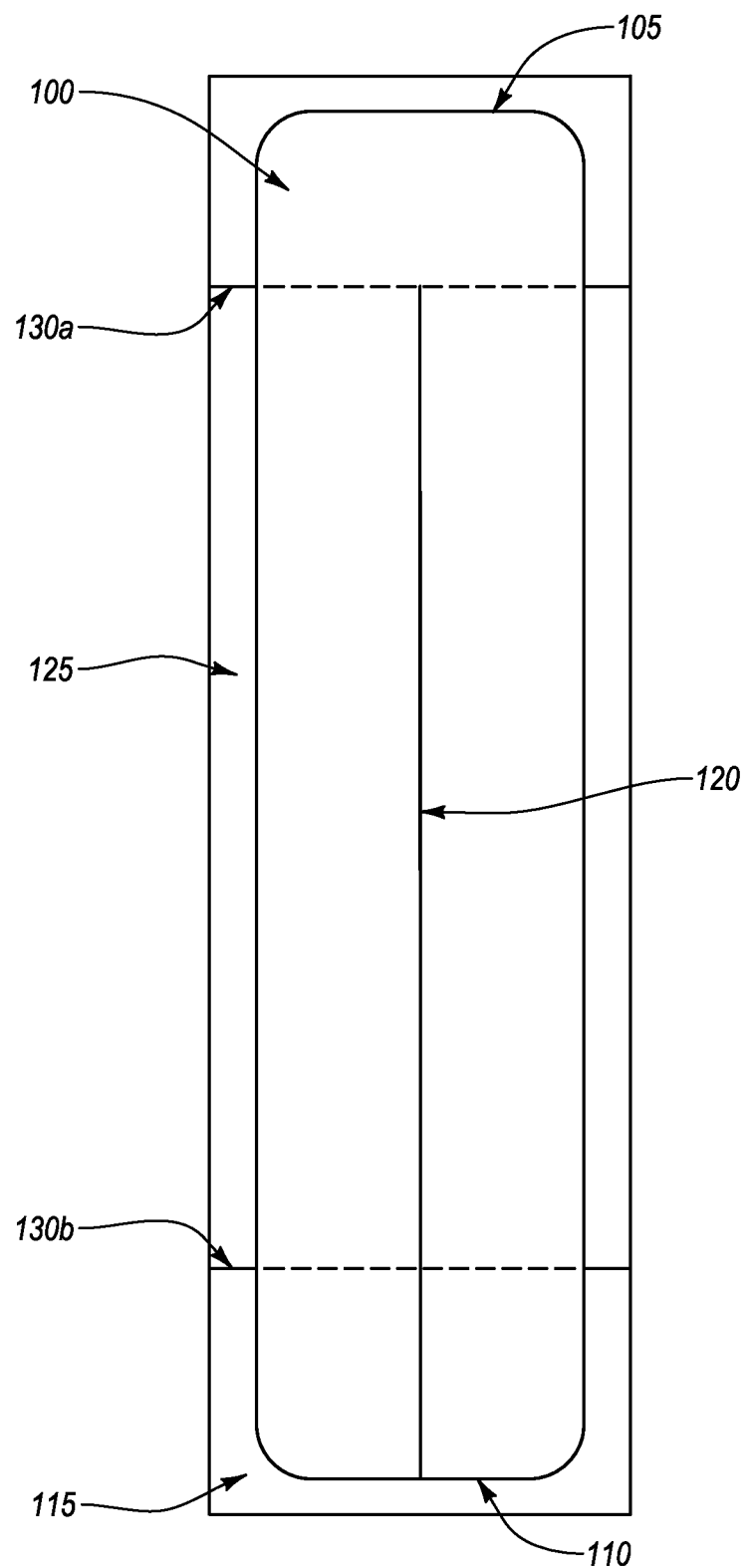
FIG. 1 illustrates an example of kinesiology tape.

FIG. 1 illustrates an example of kinesiology tape 100. In at least one implementation, kinesiology tape 100 consists of a strip of elastic and non-elastic fibers, each covered in a material which can include cotton, which is placed on human skin. The individual fibers are woven together to produce a cloth-like tape that is able to stretch in a single direction. In particular, kinesiology tape 100 is useful in therapy to reduce soreness in overused and injured muscles, in rehabilitation to accelerate recovery and in the prevention of future injury. The kinesiology tape 100 can have a lifting effect on the skin which can reduce swelling and inflammation by improving circulation and reduce pain by taking pressure off pain receptors.

FIG. 1 shows that the kinesiology tape can include an approximately rectangular shape. In particular, the kinesiology tape 100 extends in a longitudinal direction from a first end 105 to a second end 110. The width and length of the kinesiology tape 100 can be changed as desired for particular applications. For example, the width can be in the range of from about 1 inch to about 4 inches, with a width of about 2 inches being used as the illustrative example discussed herein. Similarly, typical lengths of each individual strip may be from about 5 to about 20 inches, with a length of about 10 inches being used as the illustrative example discussed herein.

FIG. 1 also shows that the corner of the kinesiology tape 100 can include a rounded corner 115. In at least one implementation, a rounded corner 115 can prevent fraying during application. Additionally or alternatively, a rounded corner 115 can reduce the chance of accidental detachment during use of the kinesiology tape 100. For example, a rounded corner 115 is much less likely than a square corner to snag on other materials, such as the user's clothing, that might detach the kinesiology tape 100 during use. Additionally or alternatively, a rounded 115 corner can provided more comfort to the user, as a rounded corner 115 does not have a sharp corner that can poke the user or otherwise cause discomfort.

FIG. 1 further shows that the kinesiology tape 100 can include a longitudinal cut 120. In at least one implementation, the longitudinal cut 120 can allow a user to split a portion of the kinesiology tape 100 when applying the kinesiology tape 100 to the user's body, as described below. The longitudinal cut 120 can extend from the second end 110 longitudinally into the body of the tape section progressing toward the first end 105. In particular, the longitudinal cut 120 can extend to a termination point prior to the first end 105, such that an uncut portion of tape is disposed at second end 110. For example, the longitudinal cut 120 can extend from the second end 110 to a point approximately two inches from the first end 105.

FIG. 1 also shows that the kinesiology tape 100 can include a backing material 125 disposed underneath the kinesiology tape 100. In at least one implementation, the backing material 125 is releasably attached to the kinesiology tape 100 by an adhesive layer, as described below. In particular, the backing material 125 can include paper or any other material suitable for protecting the adhesive on the kinesiology tape 100 from drying before use. For example, the backing material 125 can include a waxed paper which protects the adhesive from being removed or drying.

In at least one implementation, the backing material 125 may be formed as a continuous piece across its width, lacking a longitudinal cut which corresponds to the longitudinal cut 120 of the kinesiology tape 100. In particular, the lack of a longitudinal cut in the backing material 125 can allow the kinesiology tape 100 to be removed from the backing material 125 as one piece, without splitting the kinesiology tape down the longitudinal cut 120. This can allow the user to separate the two strips formed by longitudinal cut 120 or to leave the two strips formed by longitudinal cut 120 adjacent to one another, depending on the intended placement. In at least one implementation, the backing material 125 can be placed on the kinesiology tape 100 before longitudinal cut 120 is formed in the kinesiology tape 100. For example, longitudinal cut 120 may be formed by die cutting through the kinesiology tape 100 to the level of the backing material 125 to result in the described structures.

FIG. 1 shows that the backing material 125 can include a first perforation 130a and a second perforation 130b (collectively "perforations 130"). For example, the perforations 130 may be disposed at points about two inches from the first and second ends 105 and 110. In at least one implementation, the perforations 130 can facilitate the tearing of the backing material 125 along the perforations 130. In particular, perforations 120 can allow a portion of the backing material 125 to be removed from the kinesiology tape 100 while other portions of the backing material 125 remain on the kinesiology tape 100. This can facilitate placement of the kinesiology tape 100 by allowing the user to only work with desired sections of the kinesiology tape 100 or to apply the tape with a specific amount of stretch by first anchoring only the exposed adhesive and then applying the rest of the tape with desired amount of stretch.

In at least one implementation, the backing material 125 can be placed on the kinesiology tape 100 before perforations 130 are formed in the backing material 125. For example, perforations 130 may be formed by die cutting through the backing material 125 at or near the level of the kinesiology tape 100 to result in the described structures. Additionally or alternatively, the perforations can be formed in the backing material prior to the placement of the kinesiology tape 100 on the backing material 125.

Figure 2:
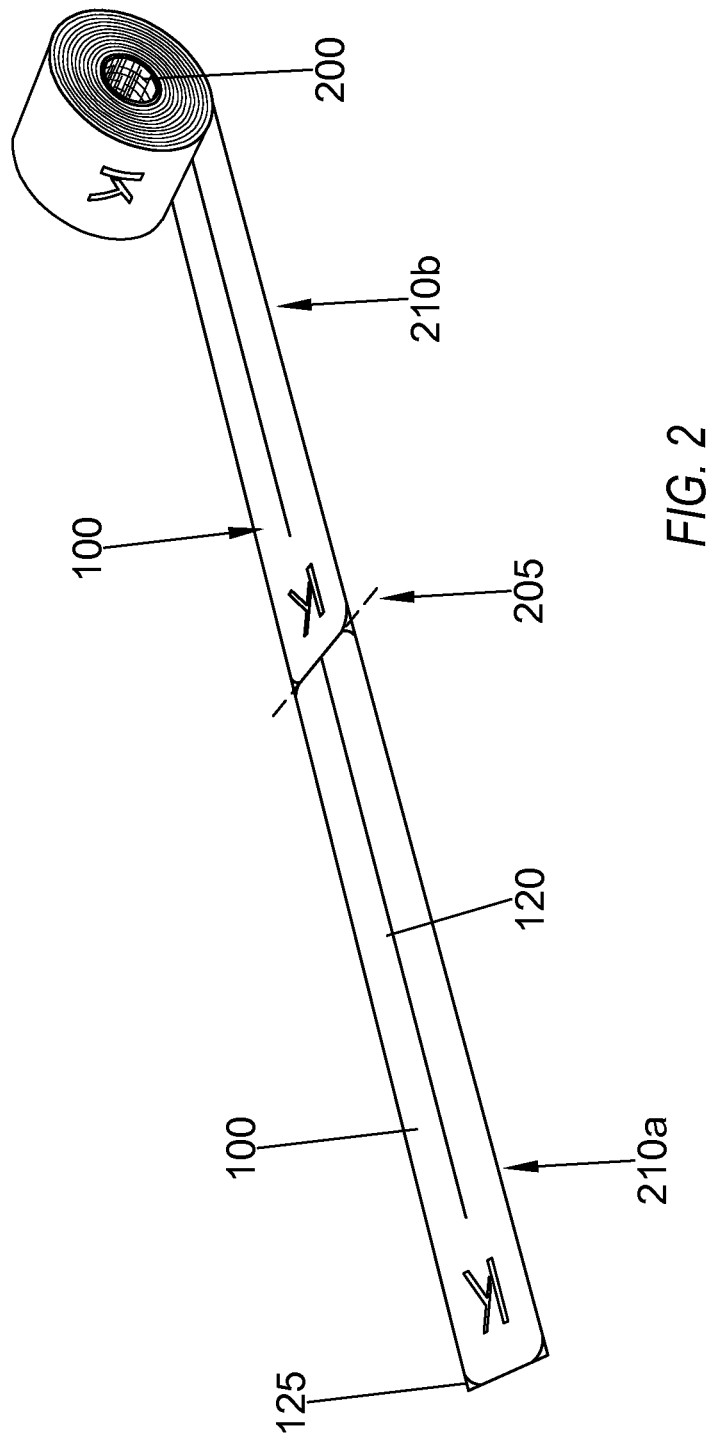
FIG. 2 illustrates a roll 200 containing individual strips of kinesiology tape.

FIG. 2 illustrates a roll 200 containing individual strips of kinesiology tape 100. In at least one implementation, a roll 200 can be used to conveniently package a number of individual strips of kinesiology tape 100 such that a user need not cut the kinesiology tape 100. In particular, the roll 200 can include pre-cut strips of kinesiology tape 100 such that the user need not cut the kinesiology tape 100 at the time of use. Additionally or alternatively, it will be appreciated that the kinesiology tape 100 can be individually packaged as individually cut sheets, or in any other form that allows the user to access an individual strip of kinesiology tape 100 without the need to cut the kinesiology tape 100, rather than on a roll.

FIG. 2 shows that the roll 200 may include multiple strips of kinesiology tape 100. For example, the roll 200 can include individual strips of kinesiology tape 100 disposed on a single strip of backing material 125. In at least one implementation, the backing material 125 can be torn by a user for the removal of a single strip of kinesiology tape 100. Additionally or alternatively, the backing material 125 can include a perforated cut 205 across its width between each individual strip of kinesiology tape 100, creating a first portion 210a of backing material and a second portion 210b of backing material and facilitating the tearing of the backing material 125 between each individual strip of kinesiology tape 100.

In at least one implementation, the backing material 125 can be cut or perforated between strips of kinesiology tape 100 by cutting the backing material 125 with suitable dies. For example, the perforations may be made by die cuts on the backing material 125 prior to the placement of kinesiology tape 100 on the backing material 125, with subsequent placement and alignment of the kinesiology tape 100. Additionally or alternatively, a large sheet of kinesiology tape 100 can be deposited on a large sheet of backing material 125 with the backing material 125 cut after placement. For example, the kinesiology tape 100 may be formed on the backing material 125 by deposition of suitable layers of the various component materials. Additionally or alternatively, the kinesiology tape 100 can be formed then adhered to the backing material 125, as described below. The sheets of kinesiology tape 100 adhered to backing material 125 can then undergo a series of trimming to arrive at the final product. For example, the kinesiology tape 100 can be trimmed to the desired width and length then cut into individual rolls 200, as described below.

Figure 3A:
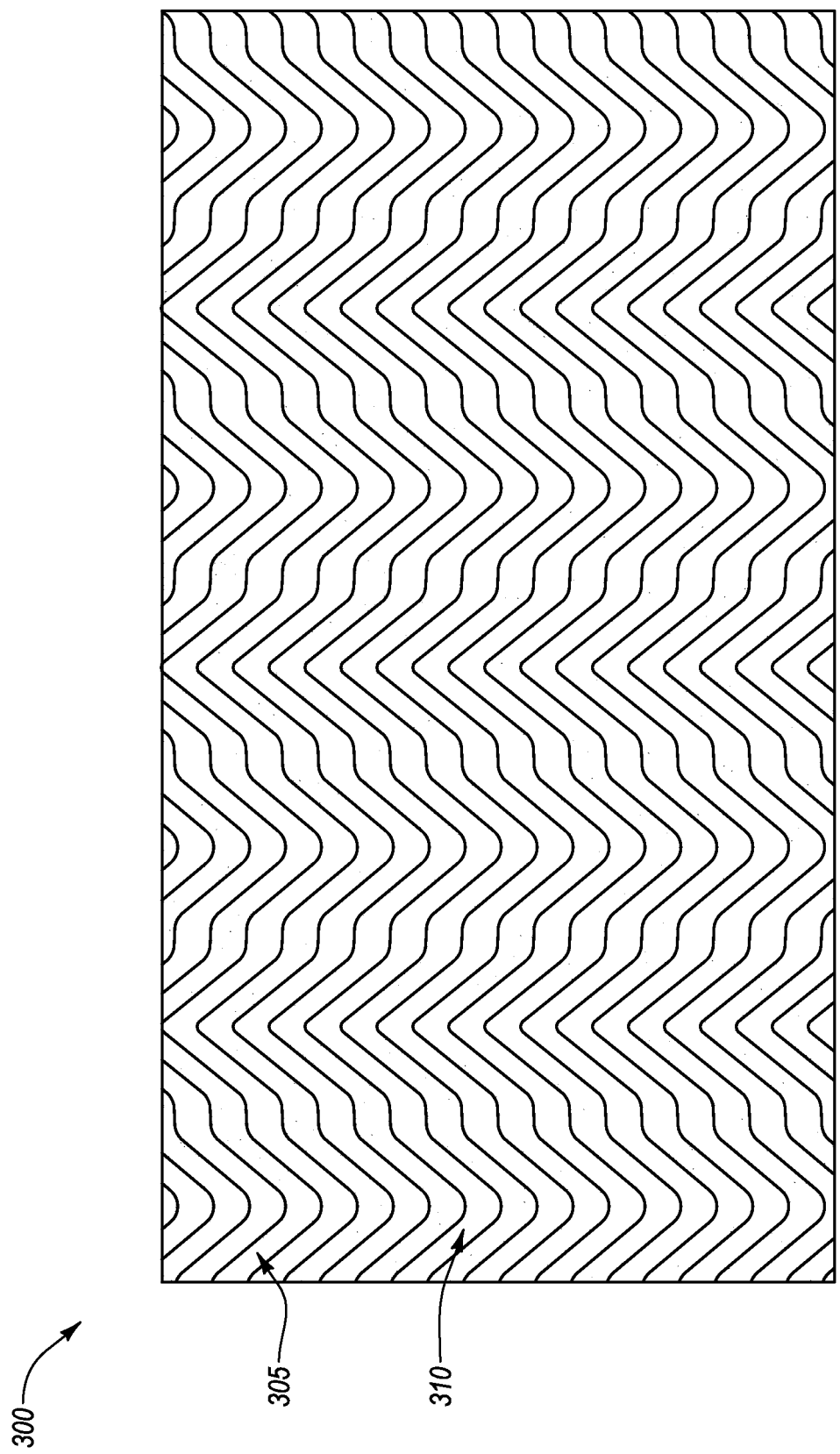
FIG. 3A illustrates an adhesive pattern for use in body-adhesive kinesiology tape.
Figure 3B:
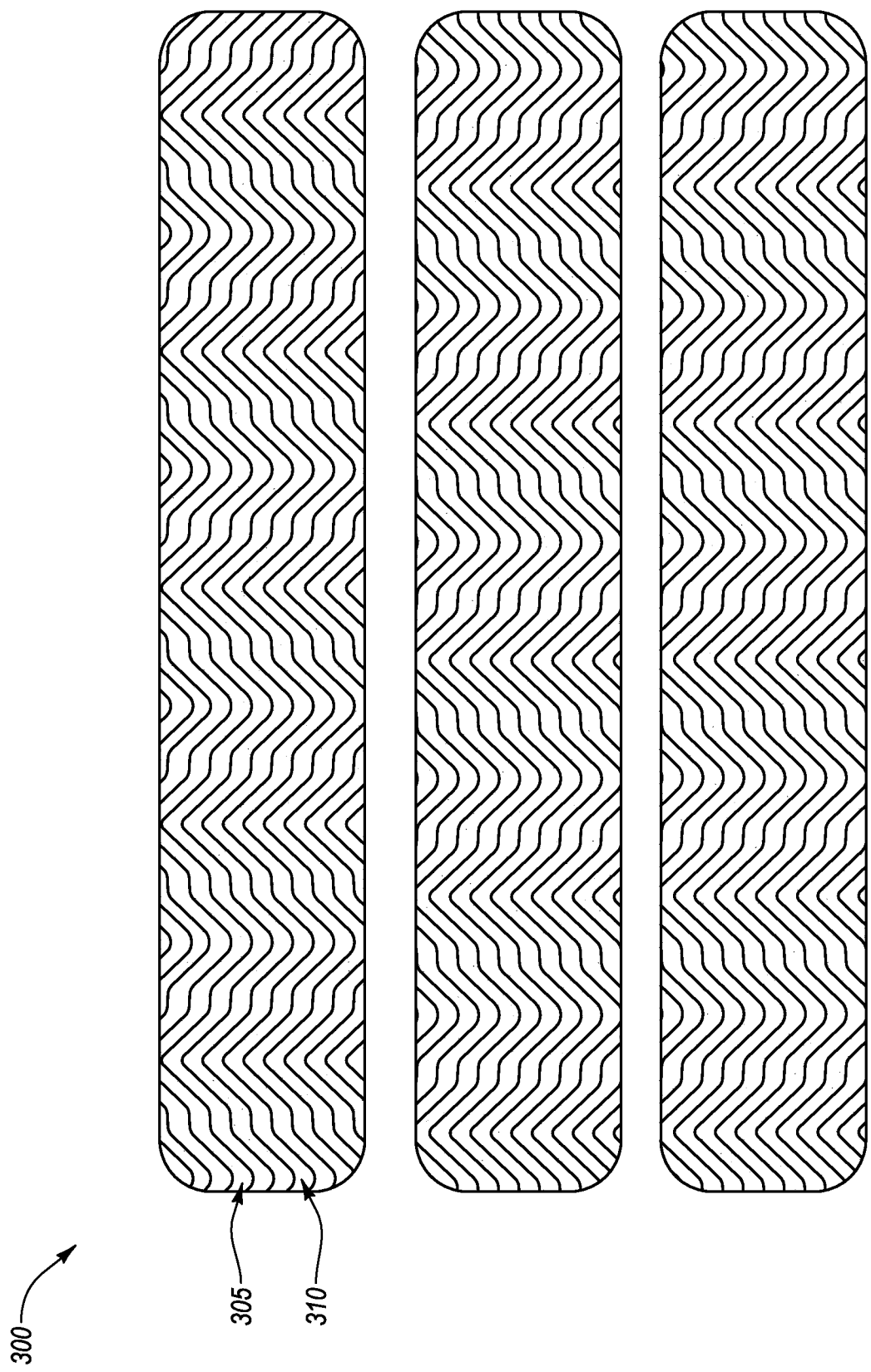
FIG. 3B illustrates the adhesive pattern of FIG. 3A after the kinesiology tape has been cut into individual strips.

FIGS. 3A and 3B illustrate an adhesive pattern 300 that can be applied to kinesiology tape. FIG. 3A illustrates the adhesive pattern applied to a sheet of kinesiology tape. FIG. 3B illustrates the adhesive pattern after the kinesiology tape has been cut into individual strips. Although described herein as deposited on kinesiology tape, one of skill in the art will understand that the adhesive can be applied to a backing material with kinesiology tape later applied to the backing material or through some other method.

In at least one implementation, the adhesive can include any adhesive which will allow the kinesiology tape to adhere to the skin of a user without irritating the user's skin. In particular, the main ingredient can include a single compound or a mixture of compounds. For example, the main ingredient can include polyacrylate. Additionally or alternatively, the adhesive can include a solvent which is configured to evaporate or break down after application of the adhesive, leaving the main ingredient behind. For example the adhesive can include about 50% of the main ingredient with the rest of the adhesive comprising solvent. In at least one implementation, the solvent can include ethyl acetate.

Additionally or alternatively, the adhesive can include pressure-sensitive adhesive. Pressure sensitive adhesive is adhesive which forms a bond when pressure is applied. I.e., no solvent, water, activator chemicals, heat or other activating agent is needed to activate the adhesive. In at least one implementation, the degree of bonding is influenced by the amount of pressure which is used to apply the adhesive to the surface of the backing material. I.e., pressure applied to the backing material and kinesiology tape in combination after the application of the adhesive can be used to activate the adhesive.

FIGS. 3A and 3B show that the adhesive pattern 300 can include a step frequency pattern. In at least one implementation, a step-frequency pattern can include the adhesive applied in a modified sine wave pattern. For example, the adhesive pattern 300 includes a wave with the upper peaks (as shown in FIG. 3) modified to include a higher amplitude that includes a sharper peak. Additionally, the adhesive pattern 300 includes lower peaks (as shown in FIG. 3) modified to include a higher absolute amplitude, i.e., a higher amplitude relative to the baseline of the sine wave. In at least one implementation, the adhesive pattern 300 can provide greater adhesion for the kinesiology tape. For example, the adhesive pattern 300 can provide adhesion even with lateral movement of the kinesiology tape relative to the user's skin. In particular, the adhesive pattern 300 can provide resistance to lateral movement of the kinesiology tape in any direction on the user's skin. In at least one implementation, such resistance can allow the kinesiology tape to better provide benefits to the user during use of the kinesiology tape, as described above.

In at least one implementation, the adhesive pattern 300 can be produced using an erratic cam. Additional information regarding the use of an erratic cam to produce an adhesive pattern is provided in U.S. patent application Ser. No. 12/554, 203, entitled "MANUFACTURE OF KINESIOLOGY TAPE," filed Sep. 4, 2009. The foregoing patent application is incorporated herein by reference in its entirety.

FIGS. 3A and 3B also show that the adhesive pattern includes a series of adhesive lines 305 interrupted by gaps 310. In at least one implementation, the gaps 310 can allow the kinesiology tape to breathe. That is, the gaps 310 can allow air to reach the skin of the user. Additionally or alternatively, the gaps 310 can allow sweat from the users skin to be wicked away from the skin by the kinesiology tape. Removing sweat from the user's skin can prevent the sweat from adversely effecting the adhesion of the kinesiology tape to the user's skin.

Figure 4:
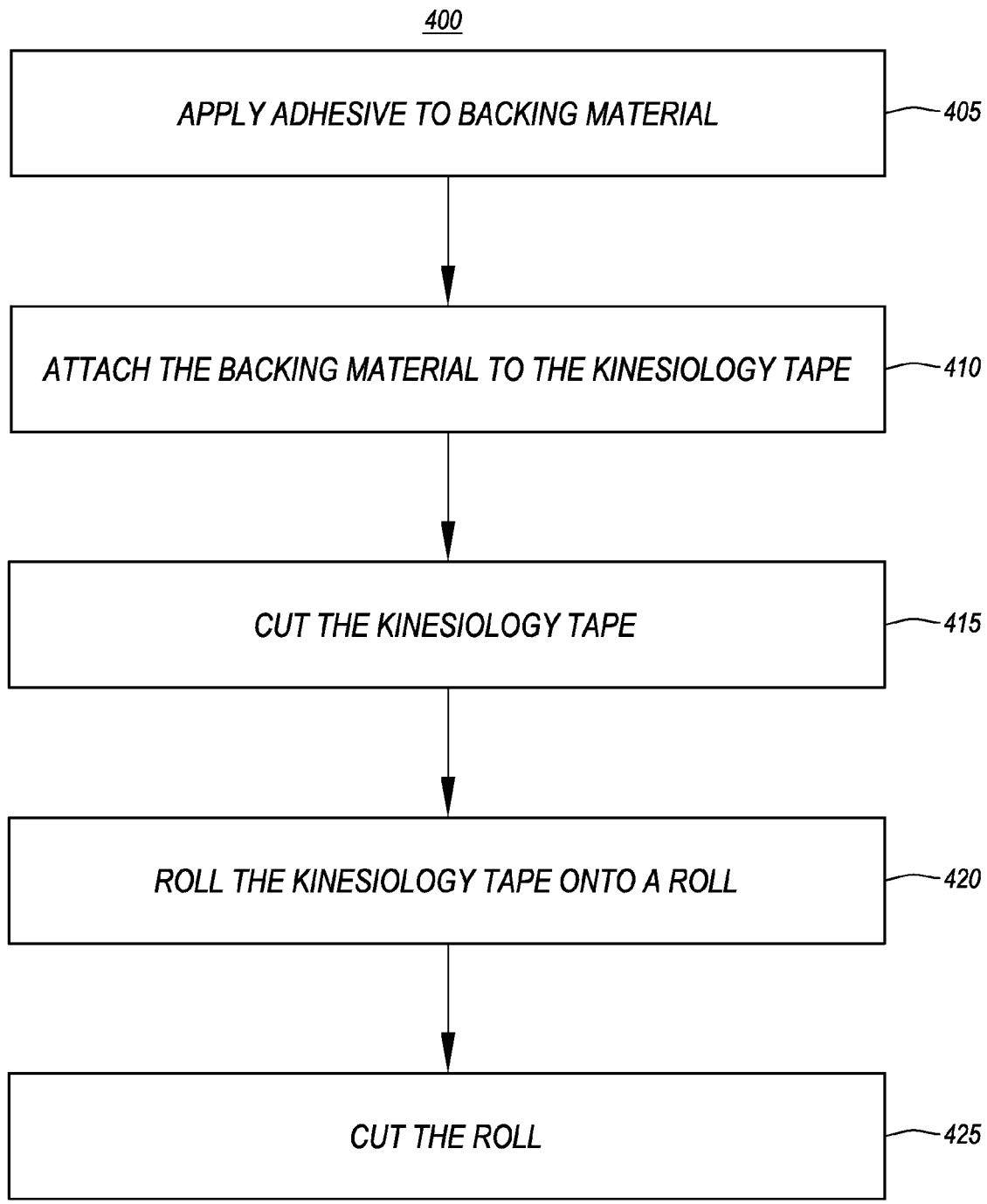
FIG. 4 is a flow chart illustrating a method for manufacturing kinesiology tape.

FIG. 4 is a flow chart illustrating a method 400 for manufacturing kinesiology tape. In at least one implementation, the kinesiology tape can be individual strips of kinesiology tape, such as the kinesiology tape 100 of FIGS. 1-3. Therefore, the method 400 will be described, exemplarily, with reference to the kinesiology tape 100 of FIG. 1-3. Nevertheless, one of skill in the art can appreciate that the method 400 can be used to produce kinesiology tape other the kinesiology tape 100 of FIG. 1-3.

FIG. 4 shows that the method 400 includes applying 405 adhesive to the backing material 125. For example, the adhesive can be applied in a step frequency pattern, such as step frequency pattern 300. In at least one implementation, the adhesive can be applied to a large sheet of backing material 125. The backing material 125 can protect the adhesive and prevent drying of the solvent until a user is ready to apply the kinesiology tape 100.

FIG. 4 also shows that the method 400 includes attaching 410 the backing material 125 to kinesiology tape 100. For example, attaching 410 the backing material 125 to kinesiology tape 100 can include pressing a strip of kinesiology tape 100 onto the backing material 125 after the application of the adhesive to the backing material 125. In at least one implementation, attaching 410 the backing material 125 to kinesiology tape 100 can include applying pressure to the kinesiology tape 100 and backing material 125 to activate a pressure sensitive adhesive, as described above.

FIG. 4 further shows that the method 400 includes cutting 415 the kinesiology tape 100. In at least one implementation, cutting 415 the kinesiology tape 100 can include using a die cut, such as a roller die. In at least one implementation, the die cut can shape and form a strip of kinesiology tape 100 and the backing material 125 attached to the kinesiology tape 100 into any desired shape. In particular, the die cut can trim a sheet of kinesiology tape 100 into large ribbons of kinesiology tape 100 and trim the large ribbons of kinesiology tape 100 into individual strips of kinesiology tape 100. Additionally or alternatively, the die cut can cut or perforate the backing material 125, allowing a user to separate individual strips of kinesiology tape 100 from one another as needed or to remove only a portion of the backing material 125, as described above.

FIG. 4 also shows that the method 400 includes rolling 420 the kinesiology tape 100 onto a roll. In at least one implementation, the sheet of backing material 125 and the individual strips of kinesiology tape 100 be rolled 420 onto a roll until the roll includes the desired number of individual strips of kinesiology tape 100 with the backing material 125 subsequently cut so that the roll includes a single strip of backing with an attached number of individual strips of kinesiology tape. For example, the roll can include any number of individual strips of kinesiology tape, such as 10, 12, 15 or 20.

In at least one implementation, the roll can include any material sufficiently strong to allow the kinesiology tape 100 to be wound around without damaging the roll. For example, the roll can include cardboard, paperboard or corrugated fiberboard. In at least one implementation, the roll allows the user to easily remove a single strip of kinesiology tape 100 and conveniently store the remaining strips of kinesiology tape 100 for later use.

FIG. 4 further shows that the method 400 further includes cutting 425 the roll. In at least one implementation, the roll can include a number of rows of individual strips of kinesiology tape 100 side-by-side. The roll can then be cut 425 into narrow rolls that include only a single strip of backing material 125 with attached kinesiology tape in a single row for packing.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 5:
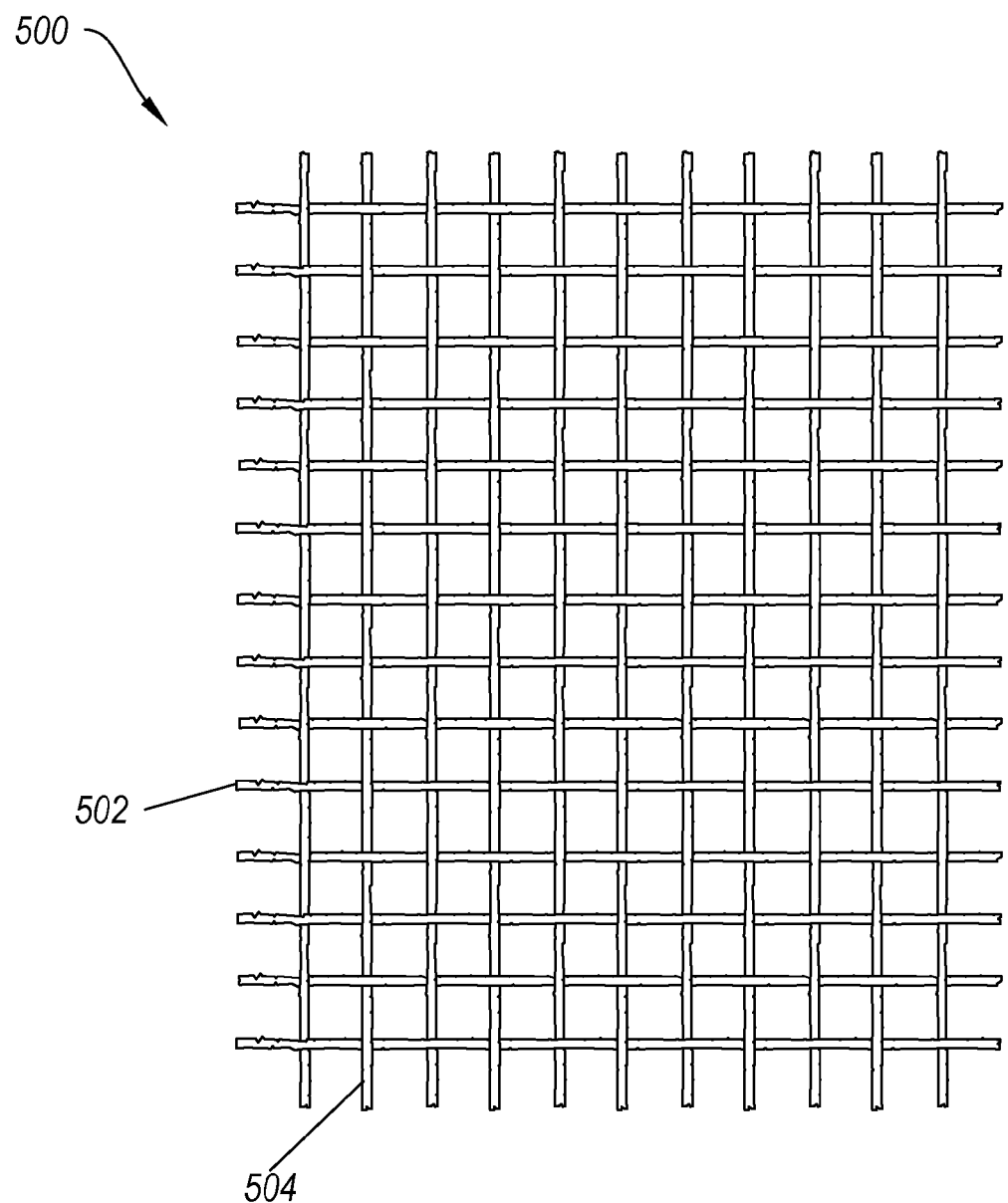
FIG. 5 illustrates an example of a weave.

FIG. 5 illustrates an example of a weave 500. FIG. 5 shows that the weave 500 can include a first set of fibers 502. FIG. 5 also shows that the weave 500 can include a second set of fibers 504. FIG. 5 further shows that the first set of fibers 502 and the second set of fibers 504 can be used to form a grid. In at least one implementation, the first set of fibers 502 and the second set of fibers 504 can be woven together.

Examples of Body-Adhesive Kinesiology Tape Applications

By way of example, and not by way of limitation, examples will be provided showing how body-adhesive kinesiology tape can be used to treat various injuries. These examples can use the kinesiology tape 100 of FIG. 1. Therefore, the example will be explained in relation to the kinesiology tape 100 of FIG. 1.

For use, the individual strips of kinesiology tape 100 can be utilized for taping a variety of body areas, without the need for a cutting implement for the kinesiology tape 100. The individual strip could be applied as a single sheet, or the uncut portion could be applied as a "anchor" portion followed by separation of the cut portion (i.e., the portion separated by longitudinal cut 120) to form various Y-shaped conformation applications. The various perforations of the backing material 125 can facilitate such placement by allowing removal of only some of the backing material 125 to expose only a portion of adhesive during application. Packages of kinesiology tape 100 can include instructions for users on the correct methods of applying the tape to various joints or other body areas.

Additionally or alternatively, individual packages of kinesiology tape 100 can be provided as targeted kits intended for the application of kinesiology tape 100 to a specific body area. Such kits can include instructions for users on the correct ways to apply the tape strips therein to the particular joint or body area targeted by that kit. For example, a kit for addressing tennis elbow can include two strips of kinesiology tape 100 and a set of instructions for the proper placement of the strips.

For segmental pain over a vertebrae or lower spinal pain the user can bend directly over with his head toward his toes. The user can tear the kinesiology tape along the longitudinal cut 120 such that the kinesiology tape 100 forms a "y". While in the bent over position, the user can place the anchor of the y shaped strip of kinesiology tape 100 at the base of the lower back with the two tails of the y pointing toward the user's anchor. The user can pull each end of the kinesiology tape 100 up along each side of the center of the user's back along each edge of the spine with low to medium tension.

For mid-line neck pain, the user can tear a five to six inch piece of kinesiology tape 100 along the longitudinal cut 120. The user can place the y shaped piece of kinesiology tape with the anchor of kinesiology tape 100 in the center of the user's back between the user's shoulder blades and pull both tails up vertically along the back and base of neck along each edge of the user's spine. The user can place a second three to four inch strip of kinesiology tape 100 from the base of lower right side of neck to opposite side with full tension in the middle but no tension on the two ends.

For lumbar spine pain in the lower back, the user can lean over slightly, as if leaning over a table. The user can place a three to four inch long strip of kinesiology tape 100 horizontally across the location of pain on the user's lower back, centering the middle of the kinesiology tape 100 over the point of pain. The first strip can be placed using middle tension. Middle tension is acquired by stretching tight the middle 2 inches of the kinesiology tape 100 and placing it firmly on the target location. The edges of the kinesiology tape 100 are then placed down without tension. Tension is found only in the center of the kinesiology tape 100. The user can place a second strip of three to four inch long kinesiology tape 100 vertically across location of pain on the user's lower back, centering the middle of the kinesiology tape 100 over the point of pain and using middle tension. The placement of the first strip and second strip can create a "+" sign. The user can place a third strip of three to four inch long kinesiology tape 100 along one of the diagonal axes of the first strip and second strip with the center of the third strip of kinesiology tape 100 over the main location of pain and using middle tension. The user can continue by placing a fourth strip of three to four inch long kinesiology tape 100 along the other diagonal axis, by once again keeping the center of kinesiology tape 100 over the point of pain and using middle tension.

For wrist extensor pain, the user can tear a sixteen to twenty inch piece of kinesiology tape 100 along the longitudinal cut 120. The user can place the anchor of the kinesiology tape 100 above the elbow and slightly on the back of the user's arm. The user can pull the ends of the kinesiology tape 100 and wrap the tails along the top of the user's forearm until the tails of the kinesiology tape 100 are slightly below the user's wrist.

For tennis elbow, the user can tear a ten to twelve inch piece of kinesiology tape 100 along the longitudinal cut 120. The user can place the anchor of the kinesiology tape 100 on the middle top of the user's forearm and pull the first tail of the kinesiology tape 100 up the user's arm. The user can pull the second tail around the user's elbow to the back of the user's elbow. The user can place a second, six to seven inch long, strip of kinesiology tape 100 with the anchor of kinesiology tape 100 right below the user's elbow on the user's forearm and wrap both ends up around the user's arm muscle.

For shin splints (also known as medial tibial stress syndrome or MTSS), the user can place a five to six inch long strip of kinesiology tape 100 with the anchor in the arch of the user's foot. The user can pull the kinesiology tape 100 up the user's leg. The kinesiology tape 100 can be placed with one edge along the interior edge of the user's tibia.

For anterior knee pain, the user can raise his/her knee slightly and place a pillow under his/her knee. The user can place a first strip of kinesiology tape 100, seven to eight inches long, horizontally right below the knee cap with middle tension. The middle of the first strip should be right below the user's knee cap. The user can tear a second, ten to eleven inch long, strip of kinesiology tape 100 along the longitudinal cut 120. The user can place the anchor of the second strip of kinesiology tape 100 on the side of the user's knee. The user can pull the first tail of the second strip along bottom of the user's knee cap and the second tail of the second strip along the top of the user's knee cap with full tension. The first tail and the second tail can cross one another on the side of the user's knee cap opposite the anchor of the second strip.

For general shoulder pain, the user can tear a ten to eleven inch strip of kinesiology tape 100 along the longitudinal cut 120. The user can place the anchor of the kinesiology tape 100 just below the user's deltoid. The user can place the first tail of the kinesiology tape 100 along front of the user's chest. The user can place the second tail of the kinesiology tape 100 around the back of the user's shoulder. The user can place a second, five to six inch long, strip of kinesiology tape 100 over the shoulder with full tension. The second strip can contact both tails of the first strip of kinesiology tape 100.

Alternatively, for general shoulder pain, the user can tear a sixteen to eighteen inch strip of kinesiology tape 100 along the longitudinal cut 120. The user can place the anchor of the strip over the user's shoulder along the boney edge of the shoulder. The anchor of the kinesiology tape 100 can be placed slightly in front of the shoulder with a two inch anchor and stretched over the shoulder with significant tension. The first tail of the kinesiology tape 100 can be stretched along the top edge of the user's scapula until it approaches the user's spine. The user can place the second tail just below the first tail.

For top of shoulder pain or AC separation the user can bend his/her elbow at a 90 degree angle and rest it on a table. The user can place a first three to four inch long strip of kinesiology tape 100 horizontally across the user's shoulder from the user's chest to the user's back using middle tension. The user can place a second strip of three to four inch long strip of kinesiology tape 100 orthogonal to the first strip using middle tension. The placement of the first strip and second strip should create a "+" sign. The user can place a third strip of three to four inch long kinesiology tape 100 along one of the diagonal axes of the first strip and second strip with the center of the third strip of kinesiology tape 100 over the shoulder using middle tension. The user can continue by placing a fourth strip of three to four inch long kinesiology tape 100 along the other diagonal axis, by once again keeping the center of kinesiology tape 100 over the shoulder and using middle tension.

For shoulder pain or neck soreness the user can flex his/her neck by stretching his/her head opposite the direction of the pain. The user can tear a five to six inch strip of kinesiology tape 100 along the longitudinal cut 120. The user can place the anchor of the kinesiology tape 100 pointed down near the top interior corner of the user's scapula. The user can pull both tails of the strip of kinesiology tape 100 up towards the neck with full tension. The user can place a second three to four inch strip of kinesiology tape 100 using full tension on the middle portion of the first strip of kinesiology tape 100 and place the second strip orthogonally across the first strip of kinesiology tape 100 with center of kinesiology tape 100 placed over the point of pain and soreness.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. Body-adhesive kinesiology tape, the body-adhesive kinesiology tape comprising individual strips of body-adhesive kinesiology tape in which a user need not cut the kinesiology tape before using, the body-adhesive kinesiology tape comprising:

a strip of pre-cut kinesiology tape, the strip of pre-cut kinesiology tape resistant to tearing and resiliently elastic, the strip of pre-cut kinesiology tape comprising a weave of fibers, at least some of the weave of fibers comprising an elastic fiber;

an adhesive on a surface of the strip of pre-cut kinesiology tape, the adhesive applied in a step frequency pattern including a plurality of steps along a longitudinal length of the strip of pre-cut kinesiology tape, the step frequency pattern including the adhesive applied in a modified sine wave pattern including a series of adhesive lines and gaps, the modified sine wave pattern including upper peaks with a higher amplitude and sharper peaks relative to a baseline of a sine wave, the modified sine wave pattern including lower peaks with a higher amplitude and sharper peaks relative to the baseline of the sine wave;

wherein the adhesive is configured to adhere the strip of pre-cut kinesiology tape to a human body; and a backing material covering the adhesive on the strip of pre-cut kinesiology tape, wherein the backing material is configured to protect the adhesive from drying until a user is ready to apply the strip of pre-cut kinesiology tape to the human body.

2. The body-adhesive kinesiology tape according to claim 1, wherein the strip of pre-cut kinesiology tape is stretchable along the longitudinal length of the strip of pre-cut kinesiology tape.

3. The body-adhesive kinesiology tape according to claim 1, further comprising a first perforation in the backing material of a strip of pre-cut kinesiology tape to facilitate tearing of the backing material and removal of a portion of the backing material while another portion of the backing material remains attached to the strip of the pre-cut kinesiology tape; and wherein the removal of the portion of the backing material facilitates anchoring of only an exposed portion of the adhesive of the strip of pre-cut kinesiology tape.

4. The body-adhesive kinesiology tape according to claim 3, further comprising a second perforation in the backing material of the strip of pre-cut kinesiology tape to facilitate tearing of the backing material.

5. The body-adhesive kinesiology tape according to claim 1, further comprising a perforation in the backing material of a strip of pre-cut kinesiology tape.

6. A roll of body-adhesive kinesiology tape comprising multiple individual, pre-cut strips of body-adhesive kinesiology tape in which a user need not cut the kinesiology tape, the roll of body-adhesive kinesiology tape comprising:

two or more individual strips of body-adhesive kinesiology tape, each of the two or more individual strips of body-adhesive kinesiology tape resistant to tearing and pre-cut, each of the two or more individual strips of the pre-cut body-adhesive kinesiology tape comprising:

a woven cloth-like strip including a first end, a second end and a longitudinal length;

an adhesive on a surface of the woven cloth-like strip, the adhesive disposed in a step frequency pattern including a plurality of steps, the step frequency pattern including a modified sine wave pattern comprising a series of adhesive lines and gaps, the modified sine wave pattern including upper peaks and lower peaks with a higher amplitude and sharper peaks relative to a baseline sine wave;

a single strip of backing material releasably attached to the two or more individual strips of pre-cut body-adhesive kinesiology tape; and a first perforation in the backing material of each individual strip of the pre-cut body-adhesive kinesiology tape to facilitate tearing of the backing material and removal of a first portion of the backing material while another portion of the backing material remains attached to the strip of the pre-cut body-adhesive kinesiology tape, the first perforation disposed between and spaced apart from opposing ends of the strip of the pre-cut body-adhesive kinesiology tape;

wherein the removal of the first portion of the backing material facilitates anchoring of only an exposed portion of the adhesive of the strip of the pre-cut body-adhesive kinesiology tape;

wherein a first strip of pre-cut body-adhesive kinesiology tape is adhered to a first portion of the backing material;

wherein a second strip of pre-cut body-adhesive kinesiology tape is adhered to a second portion of the backing material;

wherein an end of each of the two or more individual strips of pre-cut body-adhesive kinesiology tape is disposed immediately adjacent to and abuts an end of an adjacent individual strip of pre-cut body-adhesive kinesiology tape on the roll of body-adhesive kinesiology tape, the end of each individual strip of pre-cut body-adhesive kinesiology tape being separated from the end of the adjacent strip of pre-cut body-adhesive kinesiology tape solely by a single, individual cut in the body-adhesive kinesiology tape;

wherein an individual strip of pre-cut body-adhesive kinesiology tape is removed from the roll of body-adhesive kinesiology tape by tearing the backing material between the ends of the adjacent strips of the pre-cut body-adhesive kinesiology tape; and wherein the individual strip of pre-cut body-adhesive kinesiology tape is not torn when the individual strip of pre-cut body-adhesive kinesiology tape is removed from the roll of body-adhesive kinesiology tape.

7. The roll of body-adhesive kinesiology tape as in claim 6, wherein each strip of the two or more individual strips of pre-cut body-adhesive kinesiology tape is resiliently elastic.

8. The roll of body-adhesive kinesiology tape as in claim 6, wherein the first perforation in the backing material of the strip of the pre-cut body adhesive kinesiology tape is disposed at least substantially perpendicular to a longitudinal length of the pre-cut strip of body adhesive kinesiology tape.

9. The roll of body-adhesive kinesiology tape as in claim 6, wherein each individual strip of the two or more individual strips of pre-cut body-adhesive kinesiology tape includes rounded corners and the rounded corners of each individual strip of the two or more individual strips of pre-cut body-adhesive kinesiology tape are disposed immediately adjacent to the rounded corners of an adjacent individual strip of pre-cut body-adhesive kinesiology tape on the roll of body-adhesive kinesiology tape.

10. The roll of body-adhesive kinesiology tape as in claim 6, wherein each individual strip of the two or more individual strips of pre-cut body-adhesive kinesiology tape is stretchable along the longitudinal length of the strip of pre-cut body adhesive kinesiology tape.

11. The roll of body-adhesive kinesiology tape as in claim 6, wherein the first perforation in the backing material is formed by die cutting through the backing material to a level of the pre-cut body-adhesive kinesiology tape.

12. The roll of body-adhesive kinesiology tape as in claim 6, further comprising a second perforation in the backing material of each individual strip of the pre-cut body-adhesive kinesiology tape to facilitate tearing of the backing material and removal of a second portion of the backing material while another portion of the backing material remains attached to the strip of the pre-cut body-adhesive kinesiology tape, the second perforation disposed between and spaced apart from the opposing ends of the strip of the pre-cut body-adhesive kinesiology tape.

13. The roll of body-adhesive kinesiology tape as in claim 12, wherein the first perforation is disposed at least substantially perpendicular to a longitudinal length of the strip of pre-cut body-adhesive kinesiology tape; and wherein the second perforation is disposed at least substantially perpendicular to the longitudinal length of the strip of pre-cut body-adhesive kinesiology tape.

14. The roll of body-adhesive kinesiology tape as in claim 6, further comprising a longitudinal cut disposed in the woven cloth-like strip, the longitudinal cut extending a pre-determined distance along a length of the woven cloth-like strip to a termination point;
  wherein the longitudinal cut is formed by die cutting through the woven cloth-like strip to a level of the backing material.

15. Body-adhesive kinesiology tape in which a user need not cut the kinesiology tape before use, the body-adhesive kinesiology tape resistant to tearing, the body-adhesive kinesiology tape comprising:
  a strip of pre-cut kinesiology tape;
  an adhesive on a first surface of the strip of pre-cut kinesiology tape, the adhesive extending from a first end to a second end along a longitudinal length of the strip of pre-cut kinesiology tape, the adhesive comprising:
    a plurality of adhesive lines; and
    a plurality of gaps, the plurality of adhesive lines and the plurality of gaps disposed in a pattern in which a gap of the plurality of gaps is disposed between adjacent adhesive lines of the plurality of adhesive lines;
  a backing material covering the adhesive on the first surface of the strip of pre-cut kinesiology tape, the backing material configured to protect the adhesive from drying until a user is ready to apply the strip of pre-cut kinesiology tape; and
  a first perforation in the backing material to facilitate tearing of the backing material and removal of a first portion of the backing material while another portion of the backing material remains, the first perforation disposed between and spaced apart from opposing ends of the strip of pre-cut kinesiology tape, the first perforation allowing a first portion of the adhesive to be uncovered while another portion of the adhesive remains covered, the first perforation disposed at an angle to the plurality of adhesive lines and the plurality of adhesive gaps that extend along the longitudinal length of the strip of pre-cut kinesiology tape;
  wherein the adhesive is applied in a step frequency pattern including a plurality of steps along the longitudinal length of the strip of pre-cut kinesiology tape, the step frequency pattern including the adhesive applied in a modified sine wave pattern including upper peaks with a higher amplitude and sharper peaks relative to a baseline of a sine wave, the modified sine wave pattern including lower peaks with a higher amplitude and sharper peaks relative to the baseline of the sine wave.

16. The body-adhesive kinesiology tape as in claim 15, further comprising a second perforation in the backing material to facilitate tearing of the backing material and removal of a second portion of the backing material while another portion of the backing material remains, the second perforation allowing a second portion of the adhesive to be uncovered while another portion of the adhesive remains covered, the second perforation disposed at an angle to the plurality of adhesive lines and the plurality of adhesive gaps that extend along the longitudinal length of the strip of pre-cut kinesiology tape.

17. A roll of body-adhesive kinesiology tape comprising multiple individual, pre-cut strips of body-adhesive kinesiology tape on a roll, the roll of body-adhesive kinesiology tape comprising:
  a backing material disposed in a roll;
  two or more individual, pre-cut strips of body-adhesive kinesiology tape, each of the two or more individual, pre-cut strips of body-adhesive kinesiology tape resistant to tearing and pre-cut;
  an adhesive disposed on each of the two or more individual, pre-cut strips of body-adhesive kinesiology tape, the adhesive attaching the two or more individual, pre-cut strips of body-adhesive kinesiology tape to the roll of the backing material, the adhesive disposed in a step frequency pattern including a plurality of steps, the step frequency pattern including a modified sine wave pattern comprising a series of adhesive lines and gaps, the modified sine wave pattern including upper peaks and lower peaks with a higher amplitude and sharper peaks relative to a baseline sine wave; and
  a single cut separating adjacent ends of the individual, pre-cut strips of body-adhesive kinesiology tape on the roll of the backing material;
  wherein an end of each of the two or more individual, pre-cut strips of body-adhesive kinesiology tape is disposed immediately adjacent to and abuts an end of an adjacent individual, pre-cut strip of body-adhesive kinesiology tape on the roll of body-adhesive kinesiology tape, the end of each individual, pre-cut strip of body-adhesive kinesiology tape being separated from the end of the adjacent individual, pre-cut strip of body-adhesive kinesiology tape by the single cut, the single cut severing the adjacent ends of the individual, pre-cut strips of body-adhesive kinesiology tape on the roll of the backing material, the single cut not severing the backing paper between the ends of the individual, pre-cut strips of body-adhesive kinesiology tape;
  wherein an individual, pre-cut strip of body-adhesive kinesiology tape is removed from the roll of body-adhesive kinesiology tape by tearing the backing material between the ends of the adjacent individual, pre-cut strips of body-adhesive kinesiology tape; and
  wherein the individual, pre-cut strip of body-adhesive kinesiology tape is not torn when the individual strip of pre-cut body-adhesive kinesiology tape is removed from the roll of body-adhesive kinesiology tape.

* * * * *

UNITED STATES PATENT AND TRADEMARK OFFICE
CERTIFICATE OF CORRECTION

| | |
|---|---|
| PATENT NO. | : 9,308,115 B2 |
| APPLICATION NO. | : 12/626355 |
| DATED | : April 12, 2016 |
| INVENTOR(S) | : Quinn |

It is certified that error appears in the above-identified patent and that said Letters Patent is hereby corrected as shown below:

On the title page item (57), under "ABSTRACT", in Column 2, Line 1, delete "The" and insert -- Body-adhesive kinesiology tape. The --, therefor.

In the Specification

In Column 1, Line 61, delete "However" and insert -- However, --, therefor.

In Column 1, Line 62, delete "personnel" and insert -- personnel, --, therefor.

In Column 3, Line 26, delete "strips; and" and insert -- strips; --, therefor.

In Column 3, Line 28, delete "tape;" and insert -- tape; and --, therefor.

In Column 7, Line 2, delete "FIG. 1-3." and insert -- FIGS. 1-3. --, therefor.

In Column 7, Line 5, delete "FIG. 1-3." and insert -- FIGS. 1-3. --, therefor.

In Column 8, Line 24, delete "as a" and insert -- as an --, therefor.

In the Claims

In Column 10, Line 49, in Claim 1, delete "Body-adhesive" and insert -- A body-adhesive --, therefor.

In Column 13, Line 9, in Claim 15, delete "Body-adhesive" and insert -- A body-adhesive --, therefor.

Signed and Sealed this
Twelfth Day of July, 2016

Michelle K. Lee
*Director of the United States Patent and Trademark Office*